United States Patent [19]

Petrov et al.

[11] Patent Number: 5,744,616
[45] Date of Patent: Apr. 28, 1998

[54] PROCESS FOR THE PRODUCTION OF 1,4,7, 10-TETRAAZACYCLODODECANE AND ITS DERIVATIVES

[75] Inventors: Orlin Petrov; Annette Prelle; Klaus Graske; Klaus Nickisch; Bernd Radüchel; Johannes Platzek, all of Berlin, Germany

[73] Assignee: Schering Aktiengesellschaft, Berlin, Germany

[21] Appl. No.: 805,585

[22] Filed: Feb. 25, 1997

[30] Foreign Application Priority Data

Feb. 26, 1996 [DE] Germany .................. 196 08 307.9

[51] Int. Cl.$^6$ .................................................. C07D 229/02
[52] U.S. Cl. .................................................. 548/960
[58] Field of Search .................................................. 548/960

[56] References Cited

FOREIGN PATENT DOCUMENTS

| 95/31444 | 11/1995 | WIPO . |
| 96/28420 | 9/1996 | WIPO . |
| WO96/28420 | 9/1996 | WIPO . |

OTHER PUBLICATIONS

Gary R. Hansen, et al., Unique Synthesis of 1,4,7,10-Tetraazacyclododecane, p. 305, Apr. 1968.
Bradshaw et al., "Common Methods for the Formation of Polyaza Macrocycli Rings," Heterocyclic Compounds, vol. 5, pp. 126–129, 1969.

Ridha Kossai et al., "The Anodic Tetramerization of the N–Benzylaziridine: A Chain Process," Tetrahedron Letters, vol. 21, 1980, pp. 3575–3578.

Journal of the American Chemical Society, 96:7, Apr. 3, 1974, pp. 268–2270.

Sei Tsuboyama et al., Cyclic Tetramers of Optically Active Aziridines: 1,4,7,10–Tetrabenzyl–2,5,8,11–Tetra–(R–)–Ethyl–1,4,7,10–Tetraazacyclododecane, Tetrahedron Letters, No. 16, 1970, pp. 1367–1370.

Gary R. Weisman et al., "A new Synthesis of Cyclen (1,4,7,10–Tetraazacyclododecane)," *J. Org. Chem.*, vol. 61, pp. 5186–5187 (1996).

Krzysztof E. Drakowiak et al., "Synthesis of Aza–Crown Ethers," *Chem. Rev.*, vol. 89, pp. 929–972 (1989).

*Primary Examiner*—Johann Richter
*Assistant Examiner*—Ebenezer Sackey
*Attorney, Agent, or Firm*—Millen, White, Zelane, & Branigan, P.C.

[57] ABSTRACT

A process for the production of 1,4,7,10-tetraazacyclododecane (cyclene) and its derivatives on an industrial scale comprises cyclotetramerizing of benzylaziridine that is produced in situ.

14 Claims, No Drawings

PROCESS FOR THE PRODUCTION OF 1,4,7, 10-TETRAAZACYCLODODECANE AND ITS DERIVATIVES

Provisional application No. 60/032,737 filed on Dec. 16, 1996

The invention relates to a process for the production of 1,4,7,10-tetraazacyclododecane (cyclene) and its derivatives.

PRIOR ART 1,4,7,10-Tetraazacyclododecane (cyclene) is widely used both as a macrocyclic ligand and as an educt in the production of various metal-containing complexes (metal chelates) used for pharmaceutical purposes, such as, e.g., gadobutrol (INN), gadobenate (INN) or gadoteridol (INN), such as MRI contrast agents.

1,4,7,10-Tetraazacyclododecane is generally produced in the multistage synthesis process by cyclized condensation of two linear precursors (J. Chem. Rev. 1989, 929; The Chemistry of Macrocyclic Ligand Complexes, Cambridge University Press, Cambridge, U.K. 1989). Drawbacks of this method are the large number of stages, a poor total yield, and large amounts of inorganic salt waste that accumulate during synthesis.

The cyclotetramerization of N-substituted aziridines offers a method for the production of 1,4,7,10-tetraazacyclododecane that appears to be basically simpler. Variants of this reaction are described in the literature. In this case, the corresponding N-substituted aziridine is first produced from benzylethanolamine and isolated. Aziridine is then cyclotetramerized at low yield in the presence of Brønsted acids, such as, e.g., p-TsOH (J. Heterocyclic Chem. 1968, 305) or Lewis acids, such as trialkylaluminum (U.S. Pat. No. 3,828,023) or $BF_3$-etherate (Tetrahedron Letters, 1970, 1367). Although the process can be implemented only for the production of small amounts (<5 g), it is still the state of the art 16 years after the first publication (WO 95/31444).

All previously described cyclotetramerization reactions require the use of pure aziridines, which, as is generally known, have a strong mutagenic and carcinogenic action (Roth, Giftliste, VCH Weinheim). For this reason, the cyclotetramerization of aziridines, which seems to be the simplest method for the production of 1,4,7,10-tetraazacyclododecane, is virtually unused on an industrial scale. There is therefore a great deal of interest in a technically practicable process for the production of 1,4,7,10-tetraazacyclododecane that is basically environmentally benign and largely safe.

SUMMARY OF THE INVENTION

This invention provides a practicable process for the production of 1,4,7,10-tetraazacyclododecane on an industrial scale, which process overcomes the above drawbacks and in particular avoids the threat to humans posed by mutagenic and carcinogenic aziridine intermediate stages.

The process of this invention for the production of cyclene derivatives by cyclotetramerization of benzylaziridine derivatives, comprises producing the benzylaziridine derivative in situ and tetramerizing it without isolation into a tetrabenyzlcyclene derivative in the presence of a strong acid. Subsequently, the benzyl groups can be removed by hydrogenation.

Within the framework of this invention, the term cyclene derivatives is intended to comprise both 1,4,7,10-tetraazacyclododecane and those derivatives in which the ethylene bridges have alkyl substituents. The term cyclene derivative thus also relates to, for example, the compounds [2S-(2α,5α,8α,11α)]-2,5,8,11-tetramethyl-1,4,7,10-tetraazacyclododecane and [2S-(2α,5α,8α,11α)]-2,5,8,11-tetraethyl- 1,4,7,10-tetraazacyclododecane.

Analogously, the term tetrabenzylcyclene derivatives within the framework of this invention is intended to comprise both 1,4,7,10-tetrabenzyl-1,4,7,10-tetraazacyclododecane and those derivatives in which the ethylene bridges have alkyl substituents. The term benzylaziridine derivative within the framework of this invention is intended to comprise benzylaziridine and those derivatives in which the aziridine ring has alkyl substituents. The term benzylaziridine derivative thus also relates to, for example, the compounds (S)-1-benzyl-2-methyl-aziridine and (S)-1-benzyl-2-ethyl-aziridine.

The invention therefore relates to a process for the production of optionally substituted 1,4,7,10-tetraazacyclododecane derivatives by tetramerization of corresponding educts. The invention preferably relates to the production of 1,4,7,10-tetraazacyclododecane.

A preferred embodiment of the process starts from readily accessible benzylethanolamine, which can be converted by heating with concentrated sulfuric acid (e.g., 1–1.4 equivalents based on benzylethanolamine) in an organic solvent (e.g., toluene, cyclohexane, heptane, i.a.) (e.g., in a concentration of 10–20% by weight and e.g., 80°–150° C., preferably 90°–110° C.) and azeotropic distillation of the water that is produced in this case into the corresponding sulfuric acid ester (e.g., for 2–10 h). The latter is heated with an aqueous alkaline solution (e.g., NaOH, KOH; 2–5, preferably 2.5–3, equivalents based on benzylethanolamine), and the benzylaziridine that is produced in this case in a second reaction vessel, which together with the first forms a closed system, is continuously azeotropically distilled off with water. The aqueous benzylaziridine emulsion that is thus formed can, after dilution with an organic solvent (e.g., ethanol, methanol, THF), be reacted surprisingly completely to form tetrabenzylcyclene by continuous addition of 0.2–0.4, preferably 0.25–0.3, mol of a strong acid per mol of benzylaziridine (i.e., about equivalent amount of acid relative to the product). As an organic solvent, e.g., ethanol, methanol, or tetrahydrofuran (THF) can be used (typical solvent amounts are (on a weight basis), aziridine: $H_2O$: solvent=1: 5–10: 5–15; concentration of aziridine 4–10%; reaction time: 5–15 h; temperature: 50°–80° C.). As a strong acid, for example, paratoluenesulfonic acid (p-TsoH), methanesulfonic acid (MsOH), sulfuric acid, or $BF_3$-etherate can be used. The product is obtained by crystallization after the reaction mixture is alkalized (e.g., wit NaOH, KOH, etc., in an amount of 0.2–0.5 equivalent based on benzylethanolamine). If necessary, it can be further purified by recrystallization from polar solvents (e.g., THF, ethanol, methanol, isopropanol, acetone, ethylacetate, ether, furane, dioxane or mixtures thereof). The product is then hydrogenated in an organic solvent (e.g., THF, ethanol, methanol, isopropanol, with the aid of a catalyst (Pd/C)(e.g., Pd/C-amount, 5–20% related to tetrabenzylcyclene, preferably 10%; temperature 20°–50° C.; pressure 1–20 bar). After the catalyst is filtered and the solvent is distilled off, 1,4,7,10-tetraazacyclododecane is obtained at a yield of 45–60% of the theoretical total yield.

Analogously to this synthesis, alkyl-substituted benzylethanolamine can also be used, e.g., L-2-benzylaminopropanol or L-2-benzylaminobutanol, to obtain cyclene derivatives that have branches in the ethylene bridges. In a preferred embodiment of this synthesis, (S)-1-benzyl-2-methyl-aziridine is produced analogously to the above-described process from L-2-benzylaminopropanol and is reacted without isolation to form [2S-(2α,5α,8α,11α)]-2,5,8,11-tetramethyl-1,4,7,10-tetrakis(benzyl)-1,4,7,10-tetraazacyclododecane by tetramerization, from which (2S-(2α,5α,8α,11α)]-2,5,8,11-tetramethyl-1,4,7,10-tetraazacyclododecane is obtained by hydrogenation.

The process of cyclotetramerizing the benzylaziridine derivatives according to the invention differs from the process that is known in the prior art in that no isolation of the aziridine in pure form is necessary. The procedure described thus makes it possible to carry out the process in a closed system and thus to avoid the threat posed to humans and the environment by aziridine, which is carcinogenic.

In contrast to the process for cyclotetramerizing benzylaziridine that is known in the prior art, a stoichiometric amount (0.25–0.35 mol relative to one mol of benzylaziridine) is used instead of a catalytic amount of an acid (p-TsOH, MsOH, sulfuric acid, BF₃-etherate or trialkylaluminum). In tests to scale up the known process and to be able to produce large amounts of 1,4,7,10-tetraazacyclododecane in this process, only 12–25% of theoretical yield was achieved using catalytic amounts of p-TsOH in the reaction of the benzylaziridine emulsion that is produced in situ. It has now been found, surprisingly enough, that by continuously adding 0.25 to 0.35 equivalent of p-TsOH (relative to the benzylaziridine) to the azeotropically distilled-off benzylaziridine emulsion, the yield of 1,4,7,10-tetrabenzyl-1,4,7,10-tetraazacyclododecane can be improved to 60–65% of the theoretic yield at 60°–78° C. within 6–9 hours.

Other advantages of this process are the high overall yield and small amounts of waste (Na-sulfate in the case of aziridine production and toluene in the case of hydrogenation) in contrast to known processes.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application 195 08 307.9 of Feb. 26, 1996, are hereby incorporated by reference.

EXAMPLE 1

53 ml of concentrated sulfuric acid is added to a solution of 95 ml of benzylethanolamine in 690 ml of toluene. The suspension that is produced is heated to boiling for 2 hours. The water that is produced in this case (14 ml) is separated with the aid of a water separator. After cooling to 20° C., the reaction mixture is mixed with 1300 ml of water and absorptively precipitated for 10 minutes, and the organic phase is separated. Then, the aqueous phase is quickly added to a solution of 92.2 g of NaOH in 95 ml of water that is introduced in a second reaction vessel. The reaction mixture is heated to boiling. 880 g of water-N-benzylaziridine emulsion in a third reaction vessel is distilled off through a distillation bridge. The emulsion is mixed with 880 ml of ethanol and heated to 60° C. To this end, a solution of 38.0 g of p-TsOH in 19 ml of water is added within 8 hours via a metering pump. After the addition is completed, it is refluxed for two hours. Then, the reaction mixture is mixed with a solution of 12.0 g of NaOH in 20 ml of water. The precipitated product is filtered and recrystallized from 600 ml of 2:1 ethanol-THF mixture. The tetrabenzylcyclene (53 g) thus obtained is dissolved in 500 ml of isopropanol and hydrogenated with 10 g of Pd/C (10%) at 80° C. and 20 bar of H₂ pressure. After the catalyst is filtered off, the reaction solution is concentrated by evaporation, and the product is recrystallized from toluene. 15.9 g (55% of theory) of cyclene is obtained as colorless crystals. Melting point 110°–112° C.

EXAMPLE 2

95 ml of benzylethanolamine is reacted with sulfuric acid and then with NaOH, as described in Example 1. The aqueous N-benzylaziridine emulsion that is obtained is mixed with 2.6 l of ethanol and heated to 50° C. To this end, a solution of 29.3 g of p-TsOH in 15 ml of water is added within 8 hours via a metering pump. After the addition is completed, it is refluxed for two hours. Then, the reaction mixture is mixed with a solution of 9.5 g of NaOH in 20 ml of water. The precipitated product is filtered and recrystallized from 600 ml of 2:1 ethanol-THF mixture. The tetrabenzylcyclene thus obtained (55.7 g) is dissolved in 500 ml of isopropanol and hydrogenated with 10 g of Pd/C (10%) at 80° C. and 20 bar of H₂ pressure. After the catalyst is filtered off, the reaction solution is concentrated by evaporation, and the product is recrystallized from toluene. 15.9 g (58% of theory) of cyclene is obtained as colorless crystals. Melting point 111°–113° C.

EXAMPLE 3

Like Example 1, only the tetramerization is carried out with 0.33 equivalent of methanesulfonic acid. Yield 52% cyclene. Melting point 110°–112° C. Table 1:

Comparative Table on Conditions and Yields of Cyclene Synthesis by Cyclotetramerization of Benzylaziridine

| Conditions | Yield |
|---|---|
| 0.03 eq. of p-TsOH, 95% EtOH, Rfl. (analogously to Lit. 1*) | 12–25% |
| 0.33 eq. of p-TsOH, 50% EtOH, 60–80° C. (Example 1) | 55% |
| 0.25 eq. of p-TsOH, 75% EtOH, 50–80° C. (Example 2) | 58% |
| 0.33 eq. of MsOH, 50% EtOH, 70° C. (Example 3) | 52% |

*Lit. 1: J. Heterocyclic Chem. 1968, 305.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the production of a cyclene derivative by cyclotetramerization of a benzylaziridine derivative, comprising producing the benzylaziridine derivative in situ, tetramerizing it without isolation into a tetrabenzylcyclene derivative in the presence of a strong acid, and removing the benzyl groups by hydrogenation.

2. A process according to claim 1, wherein the cyclene derivative is 1,4,7,10-tetraazacyclododecane.

3. A process according to claim 1, wherein the cyclene derivative is [2S-(2α,5α,8α,11α)]-2,5,8,11-tetramethyl-1,4,7,10-tetraazacyclododecane.

4. A process according to claim 1, wherein the benzylaziridine derivative that is produced in situ is produced from benzylethanolamine.

5. A process according to claim 1, wherein the strong acid is paratoluenesulfonic acid, methanesulfonic acid, or sulfuric acid.

6. A process according to claim 1, wherein 0.25–0.35 mol of strong acid is used per mol of the benzylaziridine derivative.

7. A process of claim 6 wherein the strong acid is p-toluenesulfonic acid.

8. A process of claim 7 wherein the cyclene derivative is 1,4,7,10-tetraazacyclododecane.

9. A process of claim 7 wherein the benzylaziridine derivative that is produced in situ is produced from benzylethanolamine.

10. A process for the production of a cyclene derivative by cyclotetramerization of a benzylaziridine derivative, comprising producing the benzylaziridine derivative in situ, and tetramerizing it without isolation into a tetrabenzylcyclene derivative in the presence of a strong acid.

11. A process of preparing a cyclene derivative comprising, in the presence of a strong acid, tetramerizing the corresponding benzylaziridine derivative without isolation from a medium in which it has been in situ produced.

12. In a process for preparing a metal chelate comprising modifying a cyclene derivative to prepare a cyclene chelating agent and reacting the latter with a metal, the improvement wherein said cyclene derivative is prepared by the process of claim 1.

13. A process for cyclotetramerizing a benzylaziridine derivative comprising performing said cyclotetramerizing reaction in the presence of about at least 0.25 mole of strong acid per mole of benzylaziridine.

14. A process of claim 13 wherein the amount of strong acid is about 0.25–0.35 mole.

* * * * *